US010822302B2

(12) United States Patent
Lange et al.

(10) Patent No.: US 10,822,302 B2
(45) Date of Patent: Nov. 3, 2020

(54) METHOD OF PURIFYING PINE CHEMICAL COMPOSITIONS FROM ALDEHYDES

(71) Applicant: Kraton Polymers LLC, Houston, TX (US)

(72) Inventors: Jos H. M. Lange, Almere (NL); Mark C. Schaapman, Almere (NL)

(73) Assignee: Kraton Polymers LLC, Houston, TX (US)

( * ) Notice: Subject to any disclaimer, the term of this patent is extended or adjusted under 35 U.S.C. 154(b) by 0 days.

(21) Appl. No.: 16/695,231

(22) Filed: Nov. 26, 2019

(65) Prior Publication Data

US 2020/0165191 A1 May 28, 2020

Related U.S. Application Data

(60) Provisional application No. 62/771,223, filed on Nov. 26, 2018.

(51) Int. Cl.
*C07C 233/65* (2006.01)
*C07C 231/24* (2006.01)

(52) U.S. Cl.
CPC .......... *C07C 233/65* (2013.01); *C07C 231/24* (2013.01)

(58) Field of Classification Search
CPC .............................. C07C 233/65; C07C 231/24
See application file for complete search history.

(56) References Cited

U.S. PATENT DOCUMENTS

| 4,518,805 A | 5/1985 | Abatjoglou et al. |
| 6,274,212 B1 | 8/2001 | Rule et al. |
| 6,776,904 B2 * | 8/2004 | Zhu .......................... C02F 1/285 |
| | | 210/205 |

FOREIGN PATENT DOCUMENTS

EP  3178895 A1  6/2017

OTHER PUBLICATIONS

Mrozinski, B. A. Acetaldehyde Scavengers for Poly(ethylene terephthalate): Chemistry of Reactions, Capacity, and Modeling of Interactions. Thesis 2010 Univ.Toledo.
Suloff, E. C. Sorptoin behavior of an aliphatic series of aldelhydes in the presence of poly(ethylene terphthalate) blends containing aldehyde scavenging agents. Thesis. Chapter 5.

* cited by examiner

*Primary Examiner* — Yong L Chu
(74) *Attorney, Agent, or Firm* — Ramesh Krishnamurti

(57) ABSTRACT

A method to reduce the aldehyde content of a pine chemical composition is disclosed. The pine chemical composition is selected from gum turpentine, gum rosin, CST BLS, CTO, depitched CTO, DTO, TOH, TOR, TOP, TOFA, fractionated TOFA, TOFA dimer, TOFA trimer, TOFA monomer, isostearic acid, stearic acid, and ester- and amide derivatives thereof. The pine chemical composition is treated with an aldehyde scavenger such as anthranilamide at a temperature between 20° C. to 300° C., for 1 minute to 5 hours.

20 Claims, No Drawings

METHOD OF PURIFYING PINE CHEMICAL COMPOSITIONS FROM ALDEHYDES

RELATED APPLICATIONS

This application claims priority from U.S. Application No. 62/771,223, with a filing date of Nov. 26, 2018, the disclosure is incorporated herein by reference.

FIELD

This disclosure relates to methods to removing aldehydes from pine chemical compositions.

BACKGROUND

Pine chemical compositions can be obtained by methods such as tapping from pine trees in particular species of *Pinus*, from extraction of aged pine stumps, or can be collected in the Kraft paper pulping process as crude sulfate turpentine (CST) and crude tall oil (CTO). The presence of aldehydes in pine chemical compositions, e.g., pine resins, gum turpentine, as well as CST and CTO, and products derived thereof, can be undesirable since low molecular weight volatile aldehydes can have malodorous properties.

Pine resins as produced by tree tapping can contain cuminaldehyde. Furthermore, aldehydes can be formed by decomposition and oxidation reactions when processing pine chemical compositions at elevated temperatures. For example, at soldering temperatures over 200° C., the fumes produced when rosins break down can contain aldehydes, including formaldehyde, hexanal, acetaldehyde and cyclohexane carboxaldehyde.

Gum turpentine is the volatile oil distilled from pine resin as obtained by tapping pine trees. The solid material left behind after distillation is known as gum rosin. Gum turpentines produced by tree tapping can contain aldehyde impurities such as n-octyl aldehyde, n-nonyl aldehyde n-decyl aldehyde and higher molecular weight aldehydes such as n-dodecyl aldehyde and myristyl aldehyde.

Aldehydes are known to chemically react as electrophiles. Enolizable aldehydes can participate in chemical reactions such as aldol reactions which can contribute to thermal and oxidative chemical discoloration processes by means of chromophore formation.

There is a need to selectively purify pine chemical compositions, as well as chemical derivatives thereof, from aldehydes.

SUMMARY

A method of purifying a pine chemical composition by treatment with an aldehyde scavenger to reduce the aldehyde content at least 50% is disclosed. In one embodiment, the pine chemical is treated with one or more aldehyde scavengers in an amount of less than 6 wt. %, wherein the aldehyde scavenger is an aromatic primary amine derivative selected from: an arylamine comprising an —NH2 group and an ortho-carboxamide or an ortho-sulfonamide substituent, and an arylsulfonylhydrazide, wherein the aromatic primary amine derivative has a molecular weight less than 1000 g/mol, and comprises at least 4 elements in its molecular formula selected from the group of C, H, O, S, N, Cl, F, Br, I, B, Si and P.

In one aspect, the aldehyde scavenger is selected from the group consisting of anthranilamide, 2-aminobenzenesulfonamide, 4-amino-6-chloro-1,3-benzenedisulfonamide, 2-amino-5-bromo-benzenesulfonamide, 2-amino-5-chloro-benzenesulfonamide, 2-amino-5-methyl-benzenesulfonamide, 2,5-diamino-benzenesulfonamide, 2-amino-5-fluoro-benzenesulfonamide, 2-amino-4-chloro-benzenesulfonamide, 2-amino-4-bromo-benzenesulfonamide, 2-amino-4-methoxy-benzenesulfonamide, benzenesulfonyl hydrazide, para-toluenesulfonyl hydrazide, 2,4,6-triisopropylbenzenesulfonyl hydrazide, 2,4,6-trimethylbenzenesulfonyl hydrazide, 4-methoxybenzenesulfonyl hydrazide, 4-ethoxybenzenesulfonyl hydrazide, 4-bromobenzenesulfonyl hydrazide, 4-chlorobenzenesulfonyl hydrazide, 4-fluorobenzenesulfonyl hydrazide, 2-naphthalenesulfonyl hydrazide, 2,4-dichlorobenzenesulfonyl hydrazide, 2,5-dimethylbenzenesulfonyl hydrazide, 3-amino-2-pyridinecarboxamide, 3-amino-4-pyridinecarboxamide, 2-amino-3-pyridinecarboxamide, 3-amino-2-pyridinesulfonamide, 3-amino-4-pyridinesulfonamide, 2-amino-3-pyridinesulfonamide, and derivatives of 2-aminobenzamide wherein the phenyl ring contains 1-3 additional substituents selected from the group consisting of methyl, ethyl, tert-butyl, methoxy, ethoxy, 1-methylethoxy, cyclopropyloxy, phenylmethoxy, fluoro, chloro, bromo, iodo, trifluoromethyl, trifluoromethoxy, 4-methyl-1-piperazinyl, 3-(4-morpholinyl)propoxy, carbamoyl, nitro, amino, cyano, hydroxyl, dimethylamino, 1-piperidinyl, 1-pyrrolidinyl, 4-morpholinyl, aminosulfonyl, acetyl, carboxyl, carbomethoxy, and any combinations thereof. After treatment, the formed aldehyde-anthranilamide reaction product is optionally separated from the reaction mixture, such as by means of distillation, optionally under reduced pressure, wherein the aldehyde-anthranilamide reaction product remains in the distillation residue fraction.

DESCRIPTION

Unless defined otherwise, all technical and scientific terms used herein have the same meanings as commonly understood by one of skill in the art.

The disclosure relates to the removal of aldehyde from pine chemical feedstock by treatment with one or more aldehyde scavengers, including the scavenging of aldehydes which are formed during thermal decomposition. An aldehyde or alkanal is an organic compound containing a functional group with the structure —CHO, consisting of a carbonyl center (a carbon double-bonded to oxygen) with the carbon atom also bonded to hydrogen and to an R group, which is any generic alkyl or side chain.

Feedstock for Treatment:

The feedstock is a pine chemical composition or derived from pine chemicals. The term "pine chemical" typically refers to two main classes of chemical entities produced by pine trees, viz. turpentines and pine resins, obtained by tapping from pine trees in particular species of *Pinus*, from extraction of aged pine stumps, or can be collected in the Kraft paper pulping process as crude sulfate turpentine (CST) and crude tall oil (CTO).

In embodiments, the feedstock is selected from the group consisting of gum turpentine, gum rosin, CST BLS (black liquor soap), CTO, depitched CTO, DTO (distilled tall oil), TOH (tall oil head), TOR (tall oil rosin), TOP (tall oil pitch), TOFA (tall oil fatty acids), TOFA dimer, TOFA trimer, TOFA monomer, isostearic acid, stearic acid, and ester- and amide derivatives thereof. In embodiments, the feedstock is selected from the group consisting of BLS, CTO, depitched CTO, DTO, TOFA, TOFA dimer, TOFA trimer, TOFA monomer, isostearic acid, stearic acid, and mixtures thereof.

In yet other embodiments, the feedstock is selected from TOFA, TOFA dimer, TOFA trimer, TOFA monomer, isostearic acid, stearic acid, and combinations thereof.

In embodiments, the feedstock is selected from purified or fractionated pine chemicals, such as oleic acid fractions, linoleic acid or conjugated linoleic acids fractions obtained by purification of TOFA. In embodiments, the purity of oleic acid in fractionated TOFA is 60-99 wt %. In embodiments, the purity of linoleic acid in fractionated TOFA is 50-99 wt %. In embodiments, the purity of conjugated linoleic acids in fractionated TOFA is 40-99 wt %. The purification and fractionation methods of TOFA include chromatographic methods such as column chromatography, and SMB chromatography, and include crystallization methods, fractional evaporation and distillation methods, and membrane separation based methods.

Ester derivatives are derived from monoalcohols such as methanol or ethanol, or from a polyhydric alcohol wherein the polyhydric alcohol has 2 to 6 hydroxyl functionalities, and wherein the polyhydric alcohol comprises from 2 to 20 carbon atoms, such as ethylene glycol, diethylene glycol, triethylene glycol, glycerol, trimethylolpropane, pentaerythritol, dipentaerythritol, polyglycerol, polyglycerol-4,1,4-cyclohexanediol, or cyclohexane-1,4-dimethanol. Amide derivatives are derived from aliphatic and aromatic monoamines or diamines having 1 to 20 carbon atoms, such as n-octylamine, morpholine, piperazine, ethylenediamine, hexamethylenediamine, piperidine, pyrrolidine, and benzylamine.

Gum turpentine and CST comprise a mixture of a variety of monoterpenes, including but not limited to, alpha-pinene, beta-pinene, delta-3-carene, dipentene, limonene, phellandrene, and camphene. Fractional distillations of gum turpentine and CST can lead to the production of these monoterpenes in purified form. Freshly produced CST and freshly distilled monoterpenes from CST in general have low aldehyde content, but upon standing under the influence of external influences such as air oxygen, light, and moisture they can slowly oxidize into aldehydes.

CTO and BLS are complex mixtures which contain aldehydes as impurities, e.g., 0.1-1 wt % C20 resin aldehydes. The most prominent aldehydes in BLS and CTO are C20 cycloaliphatic resin aldehydes.

BLS mainly contains C20 resin acid salts, also sometimes referred to as rosin acid salts, such as from abietic acid as well as C16-C22 fatty acid salts like from oleic acid and linoleic acid. BLS may contain up to 5% of a neutral fraction, the so-called 'neutrals' which neutral fraction can be further divided into di- and tri-terpenes, alcohols, steroids/sterols, stilbenes and alcohols. Aldehydes in general constitute 10 wt % of this neutral fraction in BLS. The most prominent aldehydes in BLS are cycloaliphatic C20 resin aldehydes such as pimaral, sandaracopimaral, isopimaral, abietal, palustral/levopimaral, dehydroabietal and neoabietal. In general, BLS and CTO contain 0.1-1 wt % resin aldehydes. These resin aldehydes are transferred from BLS to CTO stage, depitched CTO stage, into TOH, TOFA and DTO as further outlined below.

CTO is produced from BLS by acidulation and mainly contains C20 resin acids such as from abietic acid as well as C16-C22 fatty acids. Furthermore, it contains similar neutrals as impurities as present in BLS, including 0.1-1 wt % of resin aldehydes.

CTO is in general depitched under vacuum conditions such as by wiped film evaporation or short path evaporation into a so-called depitched CTO fraction and a less volatile tall oil pitch (TOP) residue. The depitched CTO is refined on an industrial scale by fractional vacuum distillation, into several fractions, viz. tall oil heads (TOH), tall oil fatty acid (TOFA), distilled tall oil (DTO), and tall oil rosin (TOR), respectively. The resin aldehydes during this depitched CTO fractionation mainly end up in the TOH and TOFA fractions and to a lower extent in DTO. Depitched CTO mainly contains the C18-C20 acids fraction of CTO. Furthermore, it contains several neutrals as impurities, including 0.1-1 wt % of resin aldehydes.

DTO or distilled tall oil mainly consists of C20 tricyclic monocarboxylic acids known as rosin acids and C18 and C20 unsaturated fatty acids. It also can contain resin aldehydes, mostly in the range of 0.01-0.2%.

TOH or tall oil head contains saturated fatty acids like C16 palmitic acid. It generally contains resin aldehydes as impurities, generally in the range of 3-12%.

TOFA or tall oil fatty acid consists mainly of C18 unsaturated carboxylic acids, in particular oleic acid and linoleic acid. TOFA contains a range of other chemical entities in much smaller amounts, including resin aldehydes. It generally contains resin aldehydes as impurities, generally in the range of 0.2-2%. TOFA is industrially reacted into C18 monomer ("TOFA monomer"). TOFA monomer as well as isostearic acid and stearic acid, which are derived from TOFA monomer, have a higher neutrals and resin aldehydes content than TOFA which can lead to less purity in terms of their acid content.

TOFA monomer is typically a mixture of branched-, aromatic, cyclic, and straight-chain fatty acids, which may be saturated or unsaturated, and wherein the olefinic bonds in the unsaturated fatty acids can have cis- or trans-configurations. The predominant acid in TOFA monomer is "iso-oleic acid", which is actually a mixture of linear, branched and cyclic C-18 mono-unsaturated fatty acids. An example of a commercially available TOFA monomer is from Kraton Corporation, which contains both saturated and unsaturated C-18 fatty acids, with branched chain iso-oleic acids constituting the main portion, with a low level of polyunsaturated fatty acids, an acid number of 174 mg KOH/g, a Gardner color (neat) of 6.1, and an iodine number of 75 cg I/g.

In general, BLS and CTO also contain C20 rosin alcohols. C20 rosin alcohols can oxidize into C20 resin aldehydes, for example upon heating or vacuum distillation or evaporation at elevated temperatures. The thus formed C20 resin aldehydes can be removed during or after such heating, vacuum distillation or evaporation processes in the presence of an aldehyde scavenger such as anthranilamide. Examples of C20 rosin alcohols are pimarol (CAS number: 1686-59-5), and isopimarol (CAS number: 1686-64-2).

Aldehyde Scavengers:

In embodiments, the aldehyde scavengers covalently (chemically) react as nucleophile with the electrophilic aldehyde functional —CHO moiety, as the case for anthranilamide, 2-aminobenzenesulfonamide and benzenesulfonylhydrazide, or alternatively can interact by non-covalent polar interactions like hydrogen bonding to form a complex, optionally in combination with a size enclosing mechanism such as is the case for cyclodextrines like alpha-cyclodextrine. A nucleophile is a chemical species that donates an electron pair to an electrophile to form a chemical bond in relation to a reaction. Aldehyde scavengers which contain one or more nucleophilic amino (—NH2) groups in general chemically react with the electrophilic —CHO functional group of one or more aldehydes present in pine chemical compositions to form a product of higher molecular weight and lower volatility.

In embodiments, the aldehyde scavenger is selected from one or more aromatic, aliphatic or cycloaliphatic primary amine derivatives having a primary amino group and a molecular weight less than 1000 g/mol, which primary amine derivative comprises at least 3 elements in its molecular formula which are selected from the group consisting of C, H, O, S, N, Cl, F, Br, I, B, Si and P. In embodiments, the aldehyde scavenger is an aromatic primary amine derivative selected from: a) an arylamine comprising an —NH2 group and an ortho-carboxamide or an ortho-sulfonamide substituent, and b) an arylsulfonylhydrazide, wherein the aromatic primary amine derivative has a molecular weight less than 1000 g/mol, and comprises at least 4 elements in its molecular formula selected from the group of C, H, O, S, N, Cl, F, Br, and I. Aryl groups are cyclic aromatic hydrocarbons selected from monocyclic, bicyclic and tricyclic ring systems that may contain a heteroatom selected from N, O and S. Examples of aryl groups include phenyl, naphthyl, thienyl, furyl and pyridyl.

In embodiments, the aldehyde scavengers are selected from amines, preferably primary amines and derivatives thereof which contain an amino (—NH2) moiety, which amino group chemically can react with an aldehyde to form an imine derivative and water. Examples of primary amine derivatives which contain an amino moiety are anilines, monoalkylamines, hydrazines, hydrazides and sulfonylhydrazides. Primary amines and derivatives thereof can be covalently attached to a resin which can be separated after the aldehyde scavenging treatment, by methods such as filtration, decantation or centrifugation. Bisulfite salts such as $NaHSO_3$ can also form a bisulfite adduct with aldehyde groups. Polyhydric alcohols can form acetals with aldehydes. For example, reaction of sorbitol and an aromatic aldehyde such as benzaldehyde leads to the formation of dibenzylidene sorbitol.

Examples of aldehyde scavengers include, but are not limited to 2-aminobenzamide (anthranilamide), meta-xylene diamine, alpha-cyclodextrine, amino-group terminated polyamides and polyesters having a molecular weight less than 2000 g/mol, 3-aminobenzamide, 1,8-diaminonaphthalene, 2-aminobenzenesulfonamide, 4-amino-6-chloro-1,3-benzenedisulfonamide, 2-amino-5-bromo-benzenesulfonamide, 4-amino-6-(trifluoromethyl)-1,3-benzenedisulfonamide, 2-amino-5-chloro-benzenesulfonamide, 2-amino-5-methyl-benzenesulfonamide, 2,5-diamino-benzenesulfonamide, 2-amino-5-fluoro-benzenesulfonamide, 7-amino-2,3-dihydro-1,4-benzodioxin-6-sulfonamide, 2-amino-4-chloro-benzenesulfonamide, 2-amino-4-bromo-benzenesulfonamide, 2-amino-4-methoxy-benzenesulfonamide, benzene-1,2-diamine, polyacrylamide, polymethacrylamide, and copolymers of polyacrylamide and polymethacrylamide, salicyclamide, salicylanilide, o-phenylenediamine, 3,4-diaminobenzoic acid, ortho-mercaptobenzamide, malonamide, N-acetylglycinamide, 3-mercapto-1,2-propanediol, 4-amino-3-hydroxybenzoic acid, 4,5-dihydroxy-2,7-naphthalenedisulfonic acid disodium salt, biuret, allantoin, 2,3-diaminopyridine, 1,2-di aminoanthraquinone, dianilinoethane, 2-aminobenzenesulfonamide, 2-amino-2-methyl-1,3-propanediol, polymers and copolymers of allylamine, polymers and copolymers of diallylamine, polymers and copolymers of vinyl amine, poly(D-glucosamine), silica-supported polymeric amines, and amine-functionalized silica, dipropylenetriamine, tris(3-aminopropylene)amine, N,N,N'N'-tetrakis(3-aminopropyl)ethylenediamine, 1,12-dodecanediamine, amine end-capped polyethylene glycol polymers, pentaethylene hexamine (PEHA), triethylene tetraamine, polyvinyl oxazoline, D-mannitol, xylitol, D-sorbitol, 1,2-diaminocycloalkanes, choline salts, amino-functionalized ionic liquids, aminosiloxane, amino-functionalized polymers, amino-functionalized copolymers, tetraethylene pentamine, sodium bisulfite, sodium sulfite, ammonium primary phosphate, ammonium secondary phosphate, polyvinyl alcohol, adipic dihydrazide, resin-bound triamines, tosylhydrazides, tosylhydrazides linked to a resin or polystyrene polymer, tosylhydrazinoethyl-functionalized silica gel, 6-amino-1,3-benzodioxole-5-carboxamide, 3-amino-2-naphthalenecarboxamide, and derivatives of 2-aminobenzamide wherein the aromatic ring contains 1-3 additional substituents selected from the group consisting of methyl, ethyl, tert-butyl, methoxy, ethoxy, 1-methylethoxy, cyclopropyloxy, phenylmethoxy, fluoro, chloro, bromo, iodo, trifluoromethyl, trifluoromethoxy, 4-methyl-1-piperazinyl, 3-(4-morpholinyl)propoxy, carbamoyl, nitro, amino, cyano, hydroxyl, dimethylamino, 1-piperidinyl, 1-pyrrolidinyl, 4-morpholinyl, aminosulfonyl, acetyl, carboxyl, carbomethoxy, and any combinations thereof.

In embodiments, the aldehyde scavengers are selected from 2-amino-benzamide and 2-amino-benzenesulfonamide, wherein the benzene ring is optionally substituted with one or two substituents selected from the group consisting of methyl, ethyl, methoxy, fluoro, chloro, bromo, iodo, carbamoyl, nitro, amino, cyano, acetyl, carbomethoxy, sulfamoyl, and any combinations thereof.

In one embodiment, the aldehyde scavengers are selected from anthranilamide, meta-xylene diamine, 3-aminobenzamide, 1,8-diaminonaphthalene, 2-aminobenzenesulfonamide, benzene-1,2-diamine, amino-group terminated polyamides or polyesters having a molecular weight less than 2000 g/mol, 6-amino-1,3-benzodioxole-5-carboxamide, 3-amino-2-naphthalenecarboxamide, and derivatives of 2-aminobenzamide wherein the aromatic ring contains 1-3 additional substituents selected from the group consisting of methyl, ethyl, tert-butyl, methoxy, ethoxy, 1-methylethoxy, cyclopropyloxy, phenylmethoxy, fluoro, chloro, bromo, iodo, trifluoromethyl, trifluoromethoxy, 4-methyl-1-piperazinyl, carbamoyl, 3-(4-morpholinyl)propoxy, nitro, amino, cyano, hydroxyl, dimethylamino, 1-piperidinyl, 1-pyrrolidinyl, 4-morpholinyl, aminosulfonyl, acetyl, carboxyl, carbomethoxy, and any combinations thereof.

In embodiments, the aldehyde scavenger is 2-aminobenzamide (anthranilamide), due to the presence of the ortho-carboxamide moiety, forms an aldehyde-scavenger reaction product.

In embodiments, the aldehyde scavenger is an aromatic primary amine derivative selected from: an arylamine comprising an —NH2 group and an ortho-carboxamide or an ortho-sulfonamide substituent, and an arylsulfonylhydrazide, optionally substituted with 1-3 substituents selected from the group consisting of methyl, ethyl, tert-butyl, methoxy, ethoxy, 1-methylethoxy, cyclopropyloxy, isopropyl, phenylmethoxy, fluoro, chloro, bromo, iodo, trifluoromethyl, trifluoromethoxy, 4-methyl-1-piperazinyl, 3-(4-morpholinyl)propoxy, carbamoyl, nitro, amino, cyano, hydroxyl, dimethylamino, sulfamoyl, 1-piperidinyl, 1-pyrrolidinyl, 4-morpholinyl, aminosulfonyl, acetyl, carboxyl, carbomethoxy, and any combinations thereof.

In embodiments, the aldehyde scavenger is an aromatic primary amine derivative selected from: an arylamine comprising an —NH2 group and an ortho-carboxamide or an ortho-sulfonamide substituent, and an arylsulfonylhydrazide, optionally substituted with one or two substituents selected from the group consisting of methyl, ethyl, methoxy, fluoro, chloro, bromo, iodo, carbamoyl, nitro, amino, cyano, acetyl, carbomethoxy, sulfamoyl, and any combinations thereof.

In embodiments, the aryl group in the arylamine and the arylsulfonylhydrazide aldehyde scavenger represents a phenyl group.

In embodiments, the aldehyde scavenger is selected from the group consisting of anthranilamide, 2-aminobenzenesulfonamide, 4-amino-6-chloro-1,3-benzenedisulfonamide, 2-amino-5-bromo-benzenesulfonamide, 2-amino-5-chloro-benzenesulfonamide, 2-amino-5-methyl-benzenesulfonamide, 2,5-diamino-benzenesulfonamide, 2-amino-5-fluoro-benzenesulfonamide, 2-amino-4-chloro-benzenesulfonamide, 2-amino-4-bromo-benzenesulfonamide, 2-amino-4-methoxy-benzenesulfonamide, benzenesulfonyl hydrazide, para-toluenesulfonyl hydrazide, 2,4,6-triisopropylbenzenesulfonyl hydrazide, 2,4,6-trimethylbenzenesulfonyl hydrazide, 4-methoxybenzenesulfonyl hydrazide, 4-ethoxybenzenesulfonyl hydrazide, 4-bromobenzenesulfonyl hydrazide, 4-chlorobenzenesulfonyl hydrazide, 4-fluorobenzenesulfonyl hydrazide, 2-naphthalenesulfonyl hydrazide, 2,4-dichlorobenzenesulfonyl hydrazide, 2,5-dimethylbenzenesulfonyl hydrazide, 3-amino-2-pyridinecarboxamide, 3-amino-4-pyridinecarboxamide, 2-amino-3-pyridinecarboxamide, 3-amino-2-pyridinesulfonamide, 3-amino-4-pyridinesulfonamide, 2-amino-3-pyridinesulfonamide, and derivatives of 2-aminobenzamide wherein the phenyl ring contains 1-3 additional substituents selected from the group consisting of methyl, ethyl, tert-butyl, methoxy, ethoxy, 1-methylethoxy, cyclopropyloxy, phenylmethoxy, fluoro, chloro, bromo, iodo, trifluoromethyl, trifluoromethoxy, 4-methyl-1-piperazinyl, 3-(4-morpholinyl)propoxy, carbamoyl, nitro, amino, cyano, hydroxyl, dimethylamino, 1-piperidinyl, 1-pyrrolidinyl, 4-morpholinyl, aminosulfonyl, acetyl, carboxyl, carbomethoxy, and any combinations thereof.

In embodiments, the aldehyde scavenger is 2-aminobenzamide or a 2-aminobenzamide derivative having a molecular weight less than 1000 g/mol, comprising a primary amino group, a carboxamide group, and aromatic ring, and which 2-aminobenzamide derivative comprises at least 4 elements in its molecular formula which are selected from the group consisting of C, H, O, S, N, Cl, F, Br, I, B, Si and P.

In embodiments, the aldehyde scavenger is 2-aminobenzenesulfonamide or a 2-aminobenzenesulfonamide derivative having a molecular weight less than 1000 g/mol, comprising a primary amino group, a sulfonamide group, and aromatic ring, and which 2-aminobenzamide derivative comprises at least 5 elements in its molecular formula which are selected from the group consisting of C, H, O, S, N, Cl, F, Br, I, B, Si and P.

In embodiments, the aldehyde scavenger is an aromatic or aliphatic primary amine having a molecular weight less than 1000 g/mol, comprising a primary amino group, which primary amine comprises at least 3 elements in its molecular formula which are selected from the group consisting of C, H, O, S, N, Cl, F, Br, I, B, Si and P.

The aldehyde scavenger forms an irreversible covalent adduct with the aldehyde (which is removed). The stable adduct is present in the purified product and can be detected by analytical methods such as GC/MS or HTGC/MS or elemental analysis (N content increase). The aldehyde content in the treated pine chemical, if any is present, can be detected by GC/MS or by NMR.

In embodiments, the chemical reaction between an aldehyde and anthranilamide proceeds via condensation of 1 mol of aldehyde with 1 mol of to anthranilamide, followed by elimination of water and cyclization to form the corresponding 2,3-dihydro-4(1H)-quinazolinone as aldehyde-aldehyde scavenger reaction product. The reaction can be catalyzed by a suitable catalyst, for example by boric acid, para-toluenesulfonic acid and ammonium chloride. The formed 2,3-dihydro-4(1H)-quinazolinone reaction product can undergo an oxidative dehydrogenation, for example by an aerobic oxidation, into the corresponding 4(3H)-quinazolinone. Analogously, the chemical reaction between an aldehyde and 2-aminobenzenesulfonamide proceeds via condensation of 1 mol of aldehyde with 1 mol of 2-aminobenzenesulfonamide followed by elimination of water and cyclization forming the corresponding 3,4-dihydro-2H-1,2,4-benzothiadiazine 1,1-dioxide as aldehyde-aldehyde scavenger reaction product.

Treatment Method:

During heating or processing of pine chemical compositions such as gum rosin, CTO, depitched CTO, TOR, DTO, TOFA, TOH, TOP and ester- and amide derivatives thereof, at elevated temperatures in the presence of air or oxygen, and optionally light, partial decomposition and oxidation reactions can occur, wherein volatile aldehydes such as formaldehyde, hexanal, acetaldehyde, cyclohexane carboxaldehyde and other aliphatic aldehydes, can be formed. For example, the fumes produced when rosins break down at soldering temperatures over 200° C. contain volatile aldehydes.

In one embodiment, the treatment is carried out without the use of an organic solvent or catalyst. Optionally, a solvent such as acetonitrile or ethanol can be applied. Optionally, a catalyst can be applied to enhance the rate of aldehyde scavenging or as enabler to perform the aldehyde scavenging at relatively low temperatures such as at room temperature. The reaction treatment times and temperatures will depend on several parameters including but not limited to the presence of a catalyst, the use of a solvent, the state of aggregation, the degree of viscosity and polarity of the pine chemical composition.

In one embodiment, the treatment is carried within a temperature range of 50° C. to about 250° C., for 5 minutes to 24 hours, alternatively of 20° C. to 200° C., from 1 minute to 15 hours, alternatively of 120° C. to about 250° C., from 15 minutes to 5 hours, and optionally in an inert atmosphere such as under nitrogen. The formation of aldehydes during heating or processing of pine chemical compositions will depend on the decomposition temperature, in general between 120-300° C., or alternatively in the range of 150-280° C., or alternatively in the range of 170-250° C. The aldehyde scavenger is preferably added prior to occurrence of the decomposition reaction. The required minimum amount of aldehyde scavenger to be applied depends on the molecular weight of aldehyde scavengers, e.g., 136.15 g/mol for anthranilamide. In one embodiment, with an aldehyde scavenger such as anthranilamide, the aldehyde scavenger is used in an amount of 0.01-3 wt. % under heating or processing conditions within a temperature range of 120-300° C. In another embodiment, the treatment is with less than 6 wt. %, e.g., 0.03-2 wt. % or with 0.05-1 wt. %, or with 0.2-0.7 wt. %.

In one embodiment, after treatment with an aldehyde scavenger, e.g., anthranilamide, the formed aldehyde-aldehyde scavenger reaction product, e.g., aldehyde-anthranilamide reaction product, is separated from the reaction mixture. In another embodiment, the formed aldehyde-aldehyde scavenger product is separated from the reaction mixture by means of distillation, optionally under reduced pressure wherein the reaction product remains in the distillation residue fraction.

Purified Pine Chemical Product:

In one embodiment, after treatment, the aldehyde content is reduced at least 50%, In another aspect, after treatment, the aldehyde content is reduced at least 80%. In another aspect, at least 50% of the C20 resin aldehydes content in the pine chemical is removed in the treatment. In yet another aspect, at least 80% of the C20 resin aldehydes content in the pine chemical is removed in the treatment.

After treatment, the aldehyde content in the treated pine chemical is reduced to less than 1200 ppm, or less than 1000 ppm, or less than 500 ppm, or less than 250 ppm, or less than 100 ppm, or less than 50 ppm, or less than 10 ppm, or less than 5 ppm, or less than 2 ppm, or less than 1 ppm, or essentially zero, or not detectable with analytical methods known in the art such as GC/MS or NMR.

The aldehyde scavenger forms an aldehyde-scavenger reaction product in the treated/purified chemical product. In embodiments, the aldehyde-scavenger reaction product is present in the treated pine chemical composition is between 0.01 wt. % and 10 wt %, or 0.013 wt. % and 6 wt %, or 0.016 wt. % and 3 wt %, or 0.02 wt. % and 2 wt %, or 0.025 wt. % and 1 wt %, or less than 0.5 wt. %.

EXAMPLES

The following illustrative example is intended to be non-limiting.

Acid number is determined by a method according to ASTM D465-05 (2010), e.g., mass of potassium hydroxide (KOH) in milligrams required to neutralize one gram of chemical substance.

Gardner color can be measured according to the Gardner Color scale as specified in ASTM D1544-04 (2010). Gardner colors can be measured neat using a Dr. Lange LICO® 200 colorimeter.

Iodine number can be determined according to the standard methods specified in ASTM D5768-02 (2014).

Analysis of resin aldehydes content can be performed as described below:

A pine chemical sample is prepared by adding a known amount of cholesterol to serve as an internal standard for gas chromatography (GC). After weighing, acids in the sample are converted to water soluble soaps with 2N ethanolic potassium hydroxide. Once the acid fraction is converted to soap (carboxylate salts), the neutrals and unsaponifiables are isolated through liquid-liquid extraction, and dried to determine a weight-percent value. This fraction is analyzed by GC analyses. Components, including resin aldehydes, are identified based upon chromatographic retention times in conjunction with mass spectra as obtained by mass spectrometry. A Perkin-Elmer Clarus 600 Gas Chromatograph equipped with a split injection port, 60 m×0.25 mm×0.25 µm methyl polysiloxane capillary column (DB-1 type), and flame ionization detector (FID) was applied. For Gas Chromatograph-Mass Spectrometry a Perkin-Elmer Clarus 600 Gas Chromatograph was linked with a SQ8 mass detector, or a Shimadzu GC-2010 Gas Chromatograph was linked to a QP2010 Ultra mass detector.

Example 1

131.67 g crude tall oil (acid value 162 mg KOH/g) originating from United States pine forestry, having 0.62% C20 resin aldehydes content and 0.42% C20 rosin alcohols content (GC/MS analysis) was added to a 500 mL four-necked round bottom flask, equipped with thermocouple, $N_2$ gas inlet and outlet, and mechanical stirrer. A heating mantle was applied. 0.66 g anthranilamide was added to the mixture which was stirred at 350 rpm. The reaction mixture was heated at 150° C. for 1 hour. The resulting crude tall oil was analyzed by GC/MS analysis and showed 0.00% C20 resin aldehydes content (below detection limit) and 0.38% C20 rosin alcohols content. The thus obtained CTO was distilled under a reduced pressure (1 mbar). Depitched CTO was collected as the distillate (vapor temperature 100-225° C.) and showed 0.10% C20 resin aldehydes content and 0.20% C20 rosin alcohols content.

Example 2

170.92 g Tall oil fatty acid (SYLFAT™ FA1, acid value 194 mg KOH/g), having 0.5% C20 resin aldehydes content (including pimaral, isopimaral, abietal and dehydroabietal) was treated with 1.708 g anthranilamide according to the conditions of example 1. The resulting tall oil fatty acid showed 0.00% C20 resin aldehydes content.

Example 3

167.12 g Distilled tall oil (SYLVATAL™ 25/30S, acid value 189 mg KOH/g), having 0.2% C20 resin aldehydes content (including pimaral, isopimaral, abietal and dehydroabietal) was treated with 0.837 g anthranilamide according to the conditions of example 1. The resulting distilled tall oil showed 0.00% C20 resin aldehydes content.

Example 4

Depitched crude tall oil (243 g, acid value 185 mg KOH/g) having 0.31% C20 resin aldehydes content (including pimaral, isopimaral, abietal, neoabietal and dehydroabietal) was treated with 1.22 g anthranilamide according to the conditions of example 1. The resulting depitched crude tall oil showed 0.00% C20 resin aldehydes content.

Example 5

84.73 g Tall oil fatty acid (SYLFAT™ FA1, acid value 194 mg KOH/g), having 0.23% C20 resin aldehydes content (including pimaral, isopimaral, abietal, neoabietal, dehydroabietal) was treated with 0.85 g 2-amino-5-chlorobenzamide according to the conditions of example 1. The resulting tall oil fatty acid showed 0.00% C20 resin aldehydes content.

Example 6

Tall oil fatty acid (TOFA) from the same lot of SYLFAT™ FA1 was used as in Example 5 and 132.8 g TOFA was treated with 1.33 g 2-amino-benzenesulfonamide according to the conditions of example 5. The resulting tall oil fatty acid showed 0.04% C20 resin aldehydes content.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items.

As used herein, the term "comprising" means including elements or steps that are identified following that term, but any such elements or steps are not exhaustive, and an embodiment can include other elements or steps. Although the terms "comprising" and "including" have been used herein to describe various aspects, the terms "consisting essentially of" and "consisting of" can be used in place of "comprising" and "including" to provide for more specific aspects of the disclosure and are also disclosed.

Unless otherwise specified, all technical and scientific terms used herein have the same meanings as commonly understood by one of skill in the art to which the disclosed disclosure belongs. the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A method of reducing the aldehyde content of a pine chemical composition, the method comprising:
    providing an aldehyde scavenger to react with functional —CHO moiety in the aldehydes;
    treating the pine chemical composition with less than 6 wt % of the aldehyde scavenger to form an aldehyde - aldehyde scavenger reaction product;
    optionally removing the formed aldehyde - aldehyde scavenger reaction product from the treated pine chemical composition to obtain a purified pine chemical composition;
    wherein the aldehyde scavenger is an aromatic primary amine derivative
        comprising an —NH2 group and an ortho-carboxamide,
    wherein the aromatic primary amine derivative has a molecular weight less than 1000 g/mol, and comprises at least 4 elements in its molecular formula selected from the group of C, H, O, S, N, Cl, F, Br, I, B, Si and P,
    wherein the pine chemical composition is a crude tall oil (CTO), or products derived therefrom.

2. The method of claim 1, wherein the aromatic primary amine derivative is unsubstituted or substituted with 1-3 substituents selected from the group consisting of methyl, ethyl, tert-butyl, methoxy, ethoxy, 1-methylethoxy, cyclopropyloxy, isopropyl, phenylmethoxy, fluoro, chloro, bromo, iodo, trifluoromethyl, trifluoromethoxy, 4-methyl-1-piperazinyl, 3-(4-morpholinyl)propoxy, carbamoyl, nitro, amino, cyano, hydroxyl, dimethylamino, sulfamoyl, 1-piperidinyl, 1-pyrrolidinyl, 4-morpholinyl, aminosulfonyl, acetyl, carboxyl, carbomethoxy, and any combinations thereof.

3. The method of claim 1, wherein the aromatic primary amine comprising an —NH2 group and an ortho-carboxamide are optionally substituted with one or two substituents selected from the group consisting of methyl, ethyl, methoxy, fluoro, chloro, bromo, iodo, carbamoyl, nitro, amino, cyano, acetyl, carbomethoxy, sulfamoyl, and any combinations thereof.

4. The method of any of claim 1, wherein the aryl group in the aromatic primary amine derivative represents a phenyl group.

5. The method of claim 1, wherein the aldehyde scavenger is selected from the group consisting of anthranilamide, 3 amino-2-pyridinecarboxamide, 3-amino-4-pyridinecarboxamide, and derivatives of 2-aminobenzamide wherein the phenyl ring contains 1-3 additional substituents selected from the group consisting of methyl, ethyl, tert-butyl, methoxy, ethoxy, 1-methylethoxy, cyclopropyloxy, phenylmethoxy, fluoro, chloro, bromo, iodo, trifluoromethyl, trifluoromethoxy, 4-methyl-1-piperazinyl, 3-(4-morpholinyl) propoxy, carbamoyl, nitro, amino, cyano, hydroxyl, dimethylamino, sulfamoyl, 1-piperidinyl, 1-pyrrolidinyl, 4-morpholinyl, aminosulfonyl, acetyl, carboxyl, carbomethoxy, and any combinations thereof.

6. The method of claim 1, wherein at least 50% of the aldehydes is removed from the pine chemical composition.

7. The method of claim 1, wherein the aldehydes initially present in the pine chemical composition comprises C20 resin aldehydes, and wherein the C20 resin aldehydes content is reduced at least 80% after treatment.

8. The method of claim 1, wherein the treatment of the pine chemical composition with the aldehyde scavenger is at a temperature of 120-250° C.

9. The method of claim 1, wherein the aldehyde scavenger is anthranilamide.

10. The method of claim 1, wherein the pine chemical composition is treated with 0.01-3 wt % of an aldehyde scavenger.

11. The method of claim 1, wherein the wherein the pine chemical composition is treated with 0.01-3 wt % anthranilamide.

12. The method of claim 1, wherein the CTO comprises one or more of, depitched CTO, DTO, TOFA, TOFA dimer, TOFA trimer, TOFA monomer, isostearic acid, and stearic acid.

13. The method of claim 1, wherein the formed aldehyde - aldehyde scavenger reaction product removal from the treated pine chemical composition to obtain a purified pine chemical composition comprises distillation under reduced pressure, wherein the formed aldehyde-aldehyde scavenger reaction product remains in the distillation residue fraction.

14. A pine chemical composition prepared by the method of claim 1, wherein the pine chemical composition contains an aldehyde-aldehyde scavenger reaction product in an amount of between 0.01 wt. % and 10 wt %.

15. A pine chemical composition prepared by the method of claim 14, wherein the aldehyde content is less than 1200 ppm.

16. A method of reducing the aldehyde content of a pine chemical composition, the method comprising:
    treating the pine chemical composition with less than 6 wt % of anthranilamide at a temperature between 50° C. to about 250° C., for 5 minutes to 24 hours;
    wherein at least 50% of the aldehydes is removed from the pine chemical composition, and wherein the pine chemical composition is a CTO or products derived therefrom.

17. The method of claim 16, wherein the aldehydes initially present in the pine chemical composition comprises C20 resin aldehydes, wherein the C20 resin aldehydes content is reduced at least 80% after treatment, and wherein the CTO comprises one or more of depitched CTO, DTO, TOFA, TOFA dimer, TOFA trimer, TOFA monomer, isostearic acid, and stearic acid.

18. A pine chemical composition prepared by the method of claim 16, wherein the pine chemical composition contains an aldehyde-anthranilamide reaction product in an amount of between 0.01 wt. % and 10 wt %.

19. A pine chemical composition prepared by the method of claim 18, wherein the aldehyde content is less than 500 ppm.

20. A pine chemical composition prepared by the method of claim 18, wherein the aldehyde content is less than 100 ppm.

* * * * *